United States Patent [19]

Yoshida et al.

[11] Patent Number: 4,778,756
[45] Date of Patent: Oct. 18, 1988

[54] DNA COMPLEMENTARY TO RNA OF HUMAN LEUKEMIA VIRUS

[75] Inventors: Mitsuaki Yoshida; Haruo Sugano, both of Tokyo, Japan

[73] Assignee: Juridical Foundation, Japanese Foundation for Cancer Research, Tokyo, Japan

[21] Appl. No.: 104,545

[22] Filed: Oct. 5, 1987

Related U.S. Application Data

[63] Continuation of Ser. No. 816,984, Jan. 8, 1986, abandoned, which is a continuation of Ser. No. 558,800, Dec. 7, 1983, abandoned.

[30] Foreign Application Priority Data

Dec. 7, 1982 [JP] Japan ................................ 57-214287

[51] Int. Cl.$^4$ .................... C12N 15/00; C07H 15/12
[52] U.S. Cl. ................... 435/320; 435/172.3; 536/27; 935/6; 935/12; 935/32
[58] Field of Search ................... 435/172.3, 320, 317.1; 536/27

[56] References Cited

FOREIGN PATENT DOCUMENTS 0153893 2/1982 Fed. Rep. of Germany .

OTHER PUBLICATIONS

Seiki et al, 1983, "Human Adult T-Cell Leukemia Virus: Complete Nucleotide Sequence of the Provirus Genome ...", Proc. Natl. Acad. Sci., v. 80, 3618-3622.
Yoshida et al, 1982, "Isolation and Characterization of Retrovirus from Cell Lines of Human T-Cell Leukemia ...", Proc. Natl. Acad. Sci., v. 79, 2031-2035.
Seiki et al, 1982, "Human Adult T-Cell Leukemia Virus: Molecular Cloning of the Provirus and the Unique Terminal Structure", Proc. Natl. Acad. Sci., v. 79, 6899-6902.
J. Virol., vol. 38 (1981), 688:703.
P.N.A.S., vol. 79 (1982), 5680:3.

Primary Examiner—Thomas G. Wiseman
Assistant Examiner—Thomas D. Mays
Attorney, Agent, or Firm—Fitzpatrick, Cella, Harper & Scinto

[57] ABSTRACT

A viral genomic DNA and fragments thereof which are complementary to genomic RNA of human leukemia virus and a recombinant DNA molecules containing the genomic DNA or fragments thereof. The genomic DNA and fragments thereof and the recombinant DNA molecules are useful for the diagnosis, prevention and therapy of human leukemia.

2 Claims, 1 Drawing Sheet

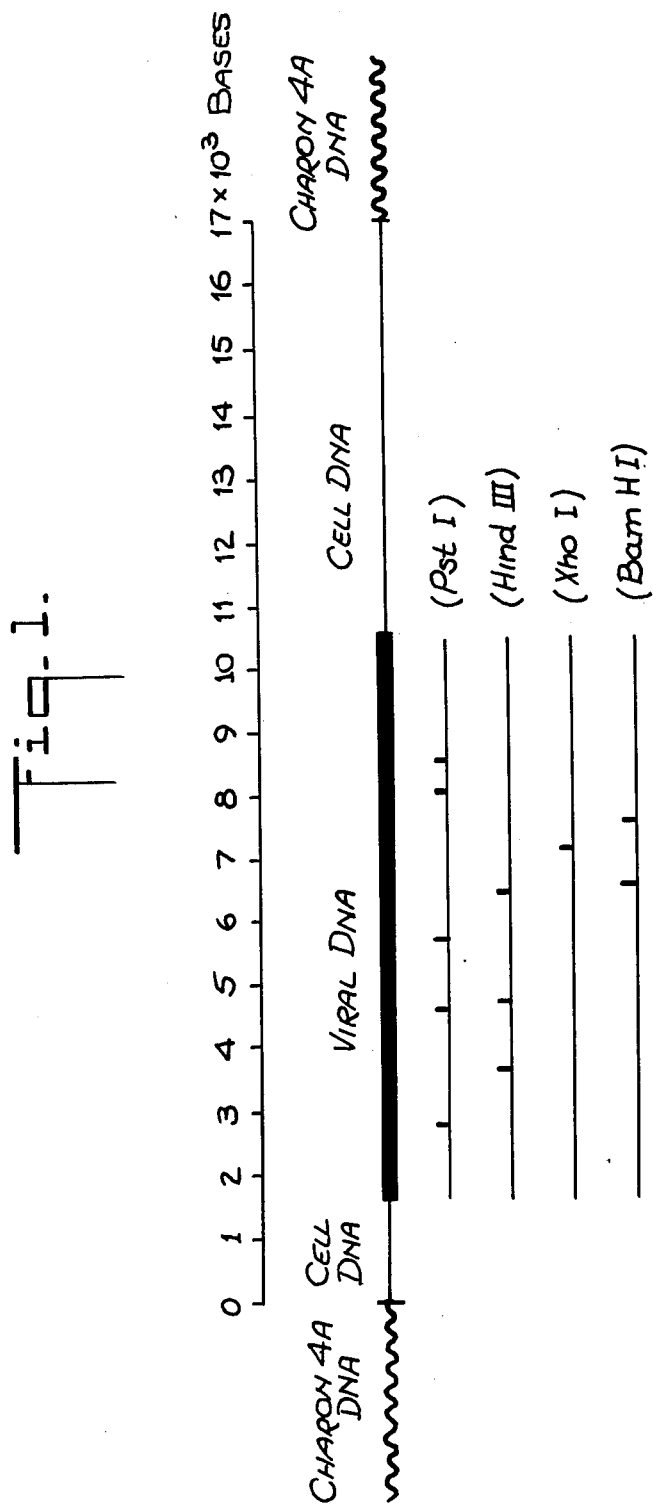

DNA COMPLEMENTARY TO RNA OF HUMAN LEUKEMIA VIRUS

This application is a continuation of application Ser. No. 816,984, filed Jan. 8, 1986, which is a continuation of application Ser. No. 558,800, filed Dec. 7, 1983, now abandoned.

BACKGROUND OF THE INVENTION

It has been reported that human leukemia virus, specifically, adult T-cell leukemia virus (referred to as ATLV hereinafter) is a retrovirus which is a case of human adult T-cell leukemia and that the provirus is integrated in the chromosome of tumor cells and cell lines established from leukemia patients (M. Yoshida, et al., Proc. Natl. Acad. Sci., USA 79, 2031, 1982). Therefore, clarification of the structure of human leukemia virus has been considered to greatly contribute to diagnosis, therapy and prevention of human leukemia and/or lymphoma. In this regard Oroszlan, et al. (Proc. Natl. Acad. Sci., USA, 79, 1291-1294, 1982) discloses the sequence of only 25 amino acids of viral protein p24 of a human leukemia virus called HTLV.

SUMMARY OF THE INVENTION

The present inventors have made studies of human leukemia virus gene and succeeded in the cloning of the provirus DNA integrated in leukemia cell DNA, which is complementary to the genomic RNA of ATLV, and the determination of the sequence of all the bases of the DNA.

The present invention relates to a DNA complementary to RNA of human leukemia virus and a recombinant DNA containing the DNA. The present invention particularly relates to a viral genomic DNA and DNA fragments thereof complementary to genomic RNA of human leukemia virus and recombinant DNA molecules containing said genomic DNA and DNA fragments respectively. The present invention furthermore relates to the use of said DNA and DNA fragments thereof as diagnostic compositions in the detection of human leukemia and/or lymphoma.

BRIEF DESCRIPTION OF THE DRAWINGS

FIG. 1 shows the restriction map of λATK-1 obtained by the present invention.

DETAILED DESCRIPTION OF THE INVENTION

As the source of DNA complementary to the genome of human leukemia virus, the DNA extracted from leukemia cells of adult T-cell leukemia patients, cell lines established from these leukemia cells, cells infected with human leukemia virus or cultured cells thereof are used. In other cases, the double stranded DNAs are synthesized from the genomic RNA of human leukemia virus using a reverse transcriptase. A preferred example is the DNA which is named ATK-1, consisting of 9,032 base pairs and obtained by extraction from adult T-cell leukemia cells isolated from peripheral blood of adult T-cell leukemia patients.

The restriction enzyme map and the entire base sequence of ATK-1 are illustrated in FIG. 1 and Table 1. ATK-1 consists of the following five important parts:

(1) LTR: The gene at both ends of the virus gene which is essential for the regulation of virus propagation and plays an important role in insertion of the provirus into the chromosomal DNA of cells. The gene consists of 754 base pairs.

(2) gag protein gene: The gene coding for the polypeptides which constitute the inner structure of the virus particle. The gene consists of 1,290 base pairs.

(3) pol gene: The gene coding for a reverse transcriptase enzyme (RNA dependent DNA polymerase) and consisting of 2,688 base pairs.

(4) env gene: The gene coding for the glycoprotein on the surface of the virus particle which is responsible for the infectivity of the virus. The gene consists of 1,464 base pairs.

(5) pX-I, pX-II, pX-III and pX-IV: These possible genes have not been clarified in respect of role and consist of 297, 261, 333 and 735 base pairs, respectively.

The above five sequence units of fragments respectively can be used as follows:

(1) LTR: Since the sequence unit is essential for the propagation of the virus and responsible for the insertion of the provirus into the cell DNA, the DNA of LTR can be used as a probe for the diagnosis of viral infection with adult T-cell leukemia virus.

(2) gag protein gene: Since the proteins encoded by the gene are produced in the largest amount, and the antibodies to these proteins and the antigens thereof are easily detectable, the gene can be used for the diagnosis of adult T-cell leukemia or viral infection.

(3) pol gene: since the gene codes for a reverse transcriptase, a specific inhibitor to the gene or gene product can be used for the prevention of infection and dispersion of the virus.

(4) env gene: Since the gene codes for a glycoprotein responsible for the infectivity of the virus, the protein of the glycoprotein can be administered in the form of a vaccine for active immunization. Therefore such gene products are most useful for the prevention of virus infection, specific destruction of leukemia cells and diagnosis of virus infection.

As illustrated in FIG. 1, ATK-1 has 5, 3, 1 and 2 cleavage sites for the restriction enzymes PstI, HindIII, XhoI and BamHI, respectively.

The DNA complementary to the genomic RNA of human leukemia virus can be recovered as a recombinant with a vector DNA. The present invention provides also the recombinant DNA.

The recombinant DNA of the present invention can be obtained by extracting DNA from adult T-cell leukemia cells of adult T-cell leukemia patients, cell lines established from these leukemia cells, cells infected with the virus or cultured cells thereof, cutting out the virus gene with restriction enzymes and inserting the gene into a vector DNA by recombinant DNA technology.

Adult T-cell leukemia cells are separated from peripheral blood of adult T-cell leukemia patients by the centrifugation method using Ficoll [A. Boyum: Scand. J. Clin. Lab. Invest. 21, 97 (1968)]. The cell lines having the gene of human leukemia virus are obtained by culturing the leukemia cells of an adult T-cell leukemia patient in the presence of a T-cell growth factor (TCGF) for a long period [B. J. Poiesz et al., Proc. Natl. Acad. Sci. USA, 77, 6815 (1980)] or by culturing the leukemia cells mixed with lymphocytes in the blood of fetal umbilical cord [I. Miyoshi et al., Nature 294, 770 (1981)]. Cells infected with the virus are also obtained by culturing the cells producing human leukemia virus mixed with human lymphocytes [I. Miyoshi et al., Gann, 72, 997 (1981), N. Yamamoto et al., Science, 217, 737 (1982)].

The cell having integrated form of human leukemia virus gene are disrupted by adding 0.5-1.0% SDS, and high molecular weight DNA and RNA are extracted with phenol, etc. The RNA is decomposed by 10-100 μg/ml RNase treatment at 37° C. for 0.5-1 hour and removed, followed by recovery of the DNA by phenol extraction. The DNA is cut by the treatment with restriction enzymes such as EcoRI, and DNA fragments of 10-20 Kb are obtained by the purification by phenol extraction. The DNA is subjected to digestion by an appropriate restriction enzyme in the presence of a buffer solution containing Tris-HCl (pH 7.0-8.5, 10-50 mM), $MgCl_2$ (5-10 mM), NaCl (0-150 mM), mercaptoethanol (0-10 mM), and the like.

Separately, phage DNA such as λ Charon 4A or an *Escherichia coli* plasmid such as pBR322 used as a vector is cut by the treatment with an appropriate restriction enzyme such as EcoRI. The resulting DNA fragments are isolated and purified by agarose gel electrophoresis.

The cell DNA fragment and the vector DNA fragment both of which are cut with the same restriction enzymes are mixed to combine both DNA fragments. The recombination reaction is carried out with T4 DNA ligase in the presence of a buffer solution containing Tris-HCl (pH 7.0-8.5, 10-50 mM), NaCl (50-150 mM), $MgCl_2$ (5-10 mM), ATP (0.05-0.2 mM) and the like at a temperature of 8°-15° C. for a period of 10-48 hours.

In the case where a phage DNA is used as the vector DNA, the recombinant DNA is recovered in the following manner.

The DNA recombined in the above-mentioned manner is reconstructed with λphage particles by, for example, the method of Blattner, et al. [Science, 202, 1279 (1978)]. *Escherichia coil* sensitive to λphage such as DR 50F [D. Piemeier, et al., Nature, 263, 526 (1976)] is infected with the reconstructed λphage particle and cultured on an agar medium to form plaques of λphages. Then, a nitrocellulose membrane is stuck on the agar medium to transfer and fix a part of the phages to the membrane. Separately, a $^{32}P$ labelled cDNA complementary to viral RNA is synthesized by, for example, the method of Yoshida, et al. [Proc. Natl. Acad. Sci., USA, 79, 2031-2035 (1982)] using the disrupted virus particles which were purified from the cells producing human leukemia viruses. The ($^{32}P$)-cDNA as a probe is hybridized with the phage DNA fixed on the nitrocellulose membrane and λphage recombinants having a gene complementary to human leukemia virus RNA are detected by autoradiography. For plaque purification the procedure described above is preferably repeated twice. Thereafter, the λphage insert is isolated and subcloned into the BamHI site of plasmid pBR322.

In the case where a plasmid DNA is used as the vector DNA, the recombinant DNA is recovered in the following manner.

The DNA recombined in the above-mentioned manner is used to transform *Escherichia coli* strains such as *Escherichia coli* χ1776 [ATCC 31244, Molecular Cloning of Recombinant DNA, Scott, W. A. & Werner, R., edited. Academic Press., p. 99-114 (1977)] and *Escherichia coli* C600 [R. K. Appleyard et al., Genetics 39, 440 (1954)] by the method of Enea, et al. [J. Mol. Biol., 96, 495-509 (1975)]. Since the recombinant plasmid carries β-lactamase gene which is harbored in the vector DNA such as *Escherichia coli* plasmid pBR322, the transformed *Escherichia coli* strains are resistant to ampicillin. Selection of a transformant containing a novel recombinant DNA harboring a DNA sequence complementary to a genomic RNA of human leukemia virus from these ampicillin-resistant strains is carried out by the same colony hybridization method with ($^{32}P$)-cDNA using a nitrocellulose membrane as in the case of phage.

The DNA complementary to RNA of human leukemia virus is recovered from the thus obtained recombinant DNA by the method of Maniatis [Cells, 15, 687 (1978)] and the base sequence thereof is determined by the method of Maxam and Gilbert [Methods in Enzymol., 65, 499 (1980)].

The DNA and recombinant DNA of the present invention are expected to be very useful for the diagnosis, prevention and therapy of human leukemia as described below.

(1) Methods of diagnosis of human leukemia and/or lymphoma and virus infection can be established using a part or the whole of the recombinant DNA.

(2) The amino acid sequence of the antigenic proteins encoded in the viral genome or fragments thereof can be determined based on the whole base sequence, and peptides or proteins containing the whole or a part of the amino acid sequence can be synthesized and produced in a large amount.

(3) Genomic DNA or fragments thereof inserted in the recombinant is reinserted in another vector DNA and propagated and amplified in bacteria or eukaryotic cells, whereby virus antigenic proteins can be produced in large amounts.

(4) The peptides or proteins produced in (2) and (3) above themselves and the antibodies against them can be used for the diagnosis, therapy and prevention of human leukemia.

Examples of the present invention are described below.

EXAMPLE 1

Cloning of integrated proviral genome of ATLV:

In this example, 0.1 ml of heparin injection as an anti-coagulant was added to 5 ml of peripheral blood taken from an adult T-cell leukemia patient for examination. The mixture was gently layered on 3 ml of Ficoll-Conray solution layer [product of Daiichi Kagaku Co.] and subjected to centrifugation at 1500 rpm ($1,200 \times g$) for 30 minutes to recover leukemia cells (about $10^8$) separated from erythrocytes. The leukemia cells are lysed in SDS (sodium dodecyl sulfate) with 1% final concentration. 200 μg/ml proteinase K (product of Merck & Co., Ltd.) was added and the mixture was incubated at 45° C. for 2 hours. Subsequently, phenol extraction was carried out three times to obtain about 0.5 mg of a high molecular weight DNA.

250 μg of the thus obtained DNA was dissolved in a buffer solution (pH 7.5) consisting of 10 mM Tris-HCl, 6 mM $MgCl_2$, 50 mM NaCl and 6 mM mercaptoethanol. 100 units of EcoRI (sold by Takara Shuzo Co.) was added and the mixture was allowed to react at 37° C. for 16 hours. The digested DNA is recovered and purified by phenol extraction carried out twice. The DNA was separated in a preparative style by 1% agarose gel electrophoresis and the fractions containing DNA fragments corresponding to a molecular size to about 11,000 to 15,000 base pairs were subjected to electrophoretical elution. Thereafter impurities were removed by phenol extraction to obtain a purified DNA. Thus, about 20 μg of a cellular DNA fragment was obtained.

Separately, 50 μg of λphage Charon 4A DNA [F. R. Blattner, Science, 196, 161 (1977)] was dissolved in 100

μl of the buffer solution mentioned above. 50 units of EcoRI was added and the mixture was allowed to react at 37° C. for 2 hours, whereby the phage DNA was cut into four DNA fragments. These fragments were separated in a preparative style by 1% agarose gel electrophoresis and two bands of larger sizes (23 Kb and 11 Kb) were cut out, followed by recovery of DNAs by the same method mentioned above. About 15 μg of phage DNA fragments was obtained from the two bands combined.

About 1 μg of the cellulose DNA fragments and about 2 μg of the Charon 4A DNA fragments obtained as mentioned above were added to 40 μl of a buffer solution (pH 7.5) containing 50 mM Tris-HCl, 10 mM MgCl$_2$, 0.1M NaCl and 0.1 mM ATP. To the mixture was added 3 units of T4 DNA ligase [product of Bethesda Research Laboratories (referred to as BRL hereinafter)] and the mixture was allowed to react at 12° C. for more than 18 hours.

The reaction mixture was then subjected to reconstruction with λphages by the method of Blattner, et al. The reconstructed λphages were added in combination with an indicator bacterium *Escherichia coli* DP 50F to an agar medium (pH 7.5) containing 10 g/l tryptone, 50 mg/l thymidine, 50 mg/l diaminopimelic acid, 2.5 g/l NaCl and 10 g/l agar, and culturing was carried out. A nitrocellulose membrane (sold by Schleicher & Schüll Co.) was stuck on the agar medium to transfer a part of phage in the plaques to the membrane and the phage DNAs were fixed by heating at 80° C. in vacuo for 120 minutes.

On the other hand, human leukemia virus particles (about 1 mg/ml as protein) purified from about 500 ml of the culture medium of the MT-2 cells which produce human leukemia cell virus [I. Miyoshi, Nature, 294, 770 (1981)] were added to 200 μl of a reaction solution consisting of 50 mM Tris-HCl, 10 mM MgCl$_2$, 1 mM dithiothreitol, 1 mM dATP, 1 mM dGTP, 1 mM dTTP, 5 μM $^{32}$P-dCTP, 50 μg/ml actinomycin D (product of Sigma), 0.02% NP40 detergent (product of Sigma) and 0.5 μg/ml oligo dT, and reaction was carried out at 37° C. for 16 hours, whereby virus $^{32}$P-cDNA complementary to human leukemia virus RNA was synthesized. The $^{32}$P-cDNA (5 × 10$^6$ cpm) was obtained after purification by alkaline tretment, phenol extraction, and Sephadex G-100 column chromatography. The $^{32}$P-cDNA was then hybridized with the λphage DNA fixed on the nitrocellulose membrane and a recombinant phage λATK-1 having the genome complementary to RNA of human leukemia virus was detected by radio-autography.

EXAMPLE 2

Preparation of insert DNA (15 Kb) for subcloning, restriction enzyme analysis and sequencing:

In this example, *Escherichia colu* DP 50F was cultured overnight in 10 ml of NZY medium consisting of 10 g/l NZ amine, 5 g/l yeast extract, 1 g/l magnesium sulfate, 50 mg/l diaminopimelic acid, 50 mg/l thymidine and 5 g/l NaCl. 10$^6$ PFU/ml recombinant phage λATK-1 obtained in Example 1 was added to the medium and culturing was further carried out overnight. The supernatant fluid of the cultured medium was used as a stock of recombinant phage. 10 ml of the stock was added to 2 l of NZY medium and culturing was carried out at 37° C. overnight. Propagated recombinant phages were purified by conventional CsCl density equilibrium centrifugation, followed by phenol extraction to obtain about 400 μg of recombinant phage DNA. The DNA was completely digested with EcoRI and subjected to 1% preparative agarose gel electrophoresis to obtain about 70 μg of inserted DNA fragment of about 15,000 base pairs.

The DNA fragment was cut with restriction enzymes such as SalI, HindIII, BamHI, PstI, SmaI, Sau3A, HinfI and HpaII and the ends of the cut fragment were labelled with $^{32}$P to determine the base sequence of the fragment according to the method of Maxam and Gilbert [Method in Enzymology, 65, 499 (1980)]. The procedures of the determination were repeated to determine the whole base sequence of a human leukemia virus gene. The result is illustrated in Table 1 which shows clearly that the human leukemia virus consists of 9,032 base pairs.

Table 1 (1)

```
  LTR
1|TGACAATGACCATGAGCCCCAAATATCCCCCGGGGCTTAGAGCCTCCCAGTGAAAACATTCCGAGAAACAGAAGTCTGAAAAGGTCA 90
GGGCCCAGACTAAGGCTCTGACGTCTCCCCCCGGAGGGCAGCTCAGCACCGGCTCGGGCTAGGCCCTGACGTGTCCCCCTGAAGACAAAT
CATAAGCTCAGACCTCCGGGAAGCCACCAAGAACCACCCATTTCCTCCCCATGTTTGTCAAGCCGTCCTCAGGCGTTGACGACAACCCCT
CACCTCAAAAAACTTTTCATGGCACGCATATGGCTCAATAAACTAGCAGGAGTCTATAAAAGCGTGGAGACAGTTCAGGAGGGGGCTCGC
ATCTCTCCTTCACGCGCCCGCCGCCCTACCTGAGGCCGCCATCCACGCCGGTTGAGTCGCGTTCTGCCGCCTCCCGCCTGTGGTGCCTCC
TGAACTGCGTCCGCCGTCTAGGTAAGTTTAAAGCTCAGGTCGAGACCGGGCCTTTGTCCGGCGCTCCCTTGGAGCCTACCTAGACTCAGC
CGGCTCTCCACGCTTTGCCTGACCCTGCTTGCTCAACTCTACGTCTTTGTTTCGTTTTCTGTTCTGCGCCGTTACAGATCGAAAGTTCCA
CCCCTTCCCTTTCATTCACGACTGACTGCCGGCTTGGCCCACGGCCAAGTACCGGCGACTCCGTTGGCTCGGAGCCAGCGACAGCCCAT
                                     LTR─┐                                           ┌─gag
CCTATAGCACTCTCAGGAGAGAAATTTAGTACACAGTTGGGGGCTCGTCCGGGATACGAGCGCCCCTTTATTCCCTAGGCAATGGCCAA
ATCTTTTCCCGTAGCGCTAGCCCTATTCCGCGACCGCCCCGGGGGCTGGCCGCTCATCACTGGCTTAACTTCCTCCAGGCGGCATATCGC 900
CTAGAACCCGGTCCCTCCAGTTACGATTTCCACCAGTTAAAAAAATTTCTTAAAATAGCTTTAGAAACACCGGCTCGGATCTGTCCCATT
AACTACTCCCTCCTAGCCAGCCTACTCCCAAAAGGATACCCCGGCCGGGTGAATGAAATTTTACACATACTCATCCAAACCCAAGCCCAG
ATCCCGTCCCGTCCCGCGCCACCGCCGCCGTCATCCCCCACCCACGACCCCCGGATTCTGATCCACAAATCCCCCCTCCCTATGTTGAG
CCTACGGCCCCCCAAGTCCTTCCAGTCATGCATCCACATGGTGCTCCTCCTAACCATCGCCCATGGCAAATGAAAGACCTACAGGCCATT
```

```
AAGCAAGAAGTCTCCCAAGCAGCCCCTGGGAGCCCCCAGTTTATGCAGACCATCCGGCTTGCGGTGCAGCAGTTTGACCCCACTGCCAAA
GACCTCCAAGACCTCCTGCAGTACCTTTGCTCCTCCCTCGTGGCTTCCCTCCATCACCAGCAGCTAGATAGCCTTATATCAGAGGCCGAA
ACCCGAGGTATTACAGGTTATAACCCATTAGCCGGTCCCCTCCGTGTCCAAGCCAACAATCCACAACAACAAGGATTAAGGCGAGAATAC
CAGCAACTCTGGCTCGCCGCCTTCGCCGCCCTGCCGGGGAGTGCCAAAGACCCTTCCTGGGCCTCTATCCTCCAAGGCCTGGAGGAGCCT
TACCACGCCTTCGTAGAACGCCTCAACATAGCTCTTGACAATGGGCTGCCAGAAGGCACGCCCAAAGACCCCATCTTACGTTCCTTAGCC
TACTCCAATGCAAACAAAGAATGCCAAAAATTACTACAGGCCCGAGGACACACTAATAGCCCTCTAGGAGATATGTTGCGGGCTTGTCAG 1800
ACCTGGACCCCCAAAGACAAAACCAAAGTGTTAGTTGTCCAGCCTAAAAAACCCCCCCAAATCAGCCGTGCTTCCGGTGCGGGAAAGCA
GGCCACTGGAGTCGGGACTGCACTCAGCCTCGTCCCCCCCCGGGCCATGCCCCCTATGTCAAGACCCAACTCACTGGAAGCGAGACTGC
CCCCGCCTAAAGCCCACTATCCCAGAACCAGAGCCAGAGGAAGATGCCCTCCTATTAGACCTCCCCGCTGACATCCCACACCCAAAAAAC
                  gag→
TCCATAGGGGGGGAGGTTTAACCTCCCCCCCCACATTACAGCAAGTCCTTCCTAACCAAGACCCAGCATCTATTCTGCCAGTTATACCGT
TAGATCCCGCCCGTCGGCCCGTAATTAAAGCCCAGGTTGACACCCAGACCAGCCACCCAAAGACTATCGAAGCTTTACTAGATACAGGAG
CAGACATGACAGTCCTTCCGATAGCCTTGTTCTCAAGTAATACTCCCTCAAAAATACATCCGTATTAGGGGCAGGGGGCCAAACCCAAGA
TCACTTTAAGCTCACCTCCCTTCCTGTGCTAATACGCCTCCCTTTCCGGACAACGCCTATTGTTTTAACATCTTGCCTAGTTGATACCAA
                                                                      ┌─pol?
AAACAACTAGGCCATCATAGGTCGTGATGCCTTACAACAATGCCAAGGCGTCCTGTACCTCCCTGAGGCAAAAAGGCCGGCCTGTAATCTT
GCCAATACAGGCGCCAGCCGTCCTTGGGCTAGAACACCTCCCAAGGCCCCCCGAAATCAGCCAGTTCCCTTTAAACCAGAACGCCTCCAG
GCCTTGCAACACTTGGTCCGGAAGGCCCTGGAGGCAGGCCATATCGAACCCTACACCGGGCCAGGGAATAACCCAGTATTCCCAGTTAAA 2700
AAGGCCAATGGAACCTGGCGATTCATCCACGACCTGCGGGCCACTAACTCTCTAACCATAGATCTCTCATCATCTTCCCCCGGGCCCCCT
GACTTGTCCAGCCTGCCAACCACACTAGCCCACTTGCAAACTATAGACCTTAGAGACGCCTTTTTCCAAATCCCCTTACCTAAACAGTTC
CAGCCCTACTTTGCTTTCACTGTCCCACAGCAGTGTAACTACGGCCCCGGCACTAGATACGCCTGGAAAGTACTACCCCAAGGGTTTAAA
AATAGTCCACCCTGTTCGAAATGCAGCTGGCCCATATCCTGCAGCCCATTCGGCAAGCTTTCCCCCAATGCACTATTCTTCAGTACATG
GATGACATTCTCCTAGCAAGCCCCTCCCATGAGGACCTACTACTACTCTCAGAGGCCACAATGGCTTCCCTAATCTCCCATGGGTTGCCT
GTGTCCGAAAACAAAACCCAGCAAACCCCTGGAACAATTAAGTTCCTAGGGCAGATAAATTTCACCCAATCACCTCACTTATGATGCAGTC
CCCACGGTACCTATACGGTCCCGCTGGGCGCTACCTGAACTTCAAGCCCTACTTGGCGAGATTCAGTGGGTCTCCAAAGGAACTCCTACC
TTACGCCAGCCCCTTCACAGTCTCTACTGTGCCTTACAAAGGCATACTGATCCCCGAGACCAAATATATTTAAATCCTTCTCAAGTTCAA
TCATTAGTGCAGCTGCGGCAGGCCCTGTCACAGAACTGCCGCAGTAGACTAGTCCAAACCCTGCCCCTCCTAGGGGCTATTATGCTGACC
CTCACTGGCACCACTACTGTAGTGTTCCAGTCCAAGCAGCAGTGGCCACTTGTCTGGCTACATGCCCCCTACCCCACACTAGCCAGTGC 3600
CCCTGGGGGCAGCTACTTGCCTCAGCTGTGTTATTACTCGACAAATACACCTTGCAATCCTATGGGCTGCTCTGCCAAACCATACATCAT
AACATCTCCACCCAAACCTTCAACCAATTCATTCAAACATCTGACCACCCCAGTGTTCCTATCTTACTCCACCACAGTCACCGATTCAAA
AATTTAGGTGCCCAAACTGGAGAACTTTGGAACACTTTTCTTAAAACAGCTGCCCCATTGGCTCCTGTGAAAGCCCTCATGCCAGTGTTT
ACTCTTTCCCCGGTGATTATAAACACCGCCCCCTGCCTGTTTTCAGACGGATCTACCTCCCGGGCAGCCTATATTCTCTGGGACAAGCAA
ATATTGTCACAAAGATCATTCCCCCTTCCGCCACCGCACAAGTCGGCCCAACGGGCCGAACTTCTCGGACTTTTGCATGGCCTCTCCAGC
GCCCGTTCGTGGCGCTGTCTCAACATATTTCTAGACTCCAAGTATCTTTATCATTACCTTCGGACCCTTGCCCTGGGCACCTTCCAAGGC
AGGTCCTCTCAGGCCCCCTTTCAGGCCCTTCTGCCCCGCTTACTATCGCGTAAGGTCGTCTATTTGCACCACGTTCGCAGCCATACCAAT
CTACCTGATCCCATCTCCAGGCTCAACGCTCTCACAGATGCCCTACTAATCACCCCTGTCCTGCAGCTCTCTCCTGCAGAACTACACAGT
TTCACCCATTGCGGACAGACGGCCCTCACATTGCAAGGGCAACCACAACTGAGGCTTCCAATATCCTGCGCTCTTGCCACGCCTGCCGC
GGAGGCAACCCACAACATCAGATGCCTCGGGGACACATCCGCCGTGGCCTACTTCCTAACCACATCTGGCAAGGCGACATTACCCATTTC 4500
AAATATAAAAATACGCTGTATCGCCTTCATGTATGGGTAGACACCCTTTTCAGGAGCCATCTCAGCTACCCAAAAGAGAAAAGAAACAAGC
TCAGAAGCTATTTCCTCTTTGCTTCAGGCCATTGCCCATCTAGGCAAGCCTAGCTACATAAACACAGACAACGGCCCTGCCTATATTTCC
CAAGACTTCCTCAATATGTGTACCTCCCTTGCTATTCGCCATACCACCCATGTCCCCTACAATCCAACCAGCTCAGGACTTGTAGAACGC
TCTAATGGCATTCTTAAAACCCTATTATATAAGTACTTTACTGACAAACCCGACCTACCCATGGATAATGCTCTATCCATAGCCCTATGG
ACAATCAACCACCTGAATGTGTTAACCAACTGCCACAAAACCCGATGGCAGCTTCACCACTCCCCCGACTCCAGCCGATCCCAGAGACA
CGTTCCCTCAGCAATAAACAAACCCATTGGTATTATTTCAAGCTTCCTGGTCTTAATAGCCGCCAGTGGAAAGGACCACAGGAGGCTCTC
```

```
CAAGAAGCTGCCGGCGCTGCTCTCATCCCGGTAAGCGCTAGTTCTGCCCAGTGGATCCCGTGGAGACTCCTCAAGCGAGCTGCATGCCCA
                                                          ┌─pol─┐┌env
AGACCCGTCGGAGGCCCCGCCGATCCCAAAGAAAAAGACCTCCAACACCATGGGTAAGTTTCTCGCCACTTTGATTTTATTCTTCCAGTT
CTGCCCCCTCATCTTCGGTGATTACAGCCCCAGCTGCTGTACTCTCACAATTGGAGTCTCCTCATACCACTCTAAACCCTGCAATCCTGC
CCAGCCAGTTTGTTCGTGGACCCTCGACCTGCTGGCCCTTCAGCAGATCAGGCCCTACAGCCCCCGTGCCCTAACCTAGTAAGTTACTC⁵⁴⁰⁰
CAGCTACCATGCCACCTATTCCCTATATCTATTCCCTCATTGGACTAAGAAGCCAAACCGAAATGGCGGAGGCTATTATTCAGCCTCTTA
TTCAGACCCTTGTTCCTTAAAGTGCCCATACCTGGGGTGCCAATCATGGACCTGCCCCTATACAGGAGCCGTCTCCAGCCCCTACTGGAA
GTTTCAACACGATGTCAATTTTACTCAAGAAGTTTCACGCCTCAATATTAATCTCCATTTTTCAAAATGCGGTTTTCCCTTCTCCCTTCT
AGTCGACGCTCCAGGATATGACCCCATCTGGTTCCTTAATACCGAACCCAGCCAACTGCCTCCCACCGCCCCTCCTCTACTCCCCCACTC
TAACCTAGACCACATCCTCGAGCCCTCTATACCATGGAAATCAAAACTCCTGACCCTTGTCCAGTTAACCCTACAAAGCACTAATTATAC
TTGCATTGTCTGTATCGATCGTGCCCAGCCTCTCCACTTGGCACGTCCTATACTCTCCCAACGTCTCTGTTCCATCCTCTTCTTCTACCCC
CCTCCTTTACCCATCGTTAGCGCTTCCAGCCCCCCACCTGACGTTACCATTTAACTGGACCCACTGCTTTGACCCCCAGATTCAAGCTAT
AGTCTCCTCCCCCTGTCATAACTCCCTCATCCTGCCCCCCTTTTCCTTGTCACCCTGTTCCCACCCTAGGATCCCGCTCCCGCCGAGCGGT
ACCGGTGGCGGTCTGGCTTGTCTCCGCCCTGGCCATGGGAGCCGGAGTGGCTGGCGGGATTACCGGCTCCATGTCCCTCGCCTCAGGAAA
GAGCCTCCTACATGAGGTGGACAAAGATATTTCCCAGTTAACTCAAGCAATAGTCAAAAACCACAAAAATCTACTCAAAATTGCGCAGTA⁶³⁰⁰
TGCTGCCCAGAACAGACGAGGCCTTGATCTCCTGTTCTGGGAGCAAGGAGGATTATGCAAAGCATTACAAGAACAGTGCCGTTTTCCGAA
TATTACCAATTCCCATGTCCCAATACTACAAGAAAGACCCCCCCTTGAGAATCGAGTCCTGACTGGCTGGGGCCTTAACTGGGACCTTGG
CCTCTCACAGTGGGCTCGAGAGGCCTTACAAACTGGAATCACCCTTGTTGCGCTACTCCTTCTTGTTATCCTTGCAGGACCATGCATCCT
                                                                                 env┐
CCGTCAGCTACGACACCTCCCCTCGCGCGTCAGATACCCCCATTACTCTCTTATAAAACCTGAGTCATCCCTGTAAACCAAGCACGCAAT
                                                                                 ┌─pX-I
TATTGCAACCACATCGCCTCCAGCCTCCCCTGCCAATAATTAACCTCTCCCATCAAATCCTCCTTCTCCTGCAGCAACTTCCTCCGTTCA
GCCTCCAAGGACTCCACCTCGCCTTCCAACTGTCTAGTATAGCCATCAATCCCCAACTCCTGCATTTTTTCTTTCCTAGCACTATGCTGT
TTCGCCTTCTCAGCCCCTTGTCTCCACTTGCGCTCACGGCGCTCCTGCTCTTCCTGCTTCCTCCTAGCGACGTCAGCGGCCTTCTTCTCC
GCCCGCCTCCTGCGCCGTGCCTTCTCCTCTTCCTTCCTTTTCAAATACTCAGCGGTCTGCTTTTCCTCCTCTTTCTCCCGCTCTTTTTTT
CGCTTCCTCTTCTCCTCAGCCCGTCGCTGCCGATCACGATGCGTTCCCCGCGAGGTGGCGCTTCTCCCCTGGAGGGCCCCGTCGCAGC
        pX-I┐
CGGCCGCGGCTTTCCTCTTCTAAGGATAGCAAACCGTCAAGCACAGCTTCCTCCTCCTCCTTGTCCTTTAACTCTTCCTCCAAGGATAAT ⁷²⁰⁰
                                                                                     ┌pX-II
AGCCCGTCCACCAATTCCTCCACCAGCAGGTCCTCCGGGCATGACACAGGCAAGCATCGAAACAGCCCTGCAGATACAAAGTTAACCATG
CTTATTATCAGCCCACTTCCCAGGGTTTGGACAGAGTCTTCTTTTCGGATACCCAGTCTACGTGTTTGGAGACTGTGTACAAGGCGACTG
GTGCCCCATCTCTGGGGGACTATGTTCGGCCCGCCTACATCGTCACGCCCTACTGGCCACCTGTCCAGAGCATCAGATCACCTGGGACCC
┌─pX-III                                                                    pX-II┐
CATCGATGGACGCGTTATCGGCTCAGCTCTACAGTTCCTTATCCCTCGACTCCCCTCCTTCCCCACCCAGAGAACCTCTAAGACCCTCAA
                                                     ┌─pX-IV
GGTCCTTACCCCGCCAATCACTCATACAACCCCCAACATTCCACCCTCCTTCCTCCAGGCCATGCGCAAATACTCCCCCTTCCGAAATGG
ATACATGGAACCCACCCTTGGGCAGCACCTCCCAACCCTGTCTTTTCCAGACCCCGGACTCCGGCCCCAAAACCTGTACACCCTCTGGGG
                                                      pX-III┐
AGGCTCCGTTGTCTGCATGTACCTCTACCAGCTTTCCCCCCCCATCACCTGGCCCCTCCTGCCCCACGTGATTTTTTGCCACCCCGGCCA
GCTCGGGGCCTTCCTCACCAATGTTCCCTACAAGCGAATAGAAGAACTCCTCTATAAAATTTCCCTCACCACAGGGGCCCTAATAATTCT
ACCCGAAGACTGTTTGCCCACCACCCTTTTCCAGCCTGCTAGGGCACCCGTCACGCTAACAGCCTGGCAAAACGGCCTCCTTCCGTTCCA
CTCAACCCTCACCACTCCAGGCCTTATTTGGACATTTACCGATGGCACGCCTATGATTTCCGGGCCCTGCCCTAAAGATGGCCAGCCATC ⁸¹⁰⁰
TTTAGTACTACAGTCCTCCTCCTTTATATTTCACAAATTTCAAACCAAGGCCTACCACCCCTCATTTCTACTCTCACACGGCCTCATACA
                                                                                 ┌─LTR
GTACTGTTCCTTTCATAGTTTACATCTCCTGTTTGAAGAATACACCAACATCCCCATTTCTCTACTTTTTAACGAAAAAGAGGCAGATGA
                                                   pX-IV┐
CAATGACCATGAGCCCCAAATATCCCCCGGGGGCTTAGAGCCTCCCAGTGAAAAACATTTCCGAGAAACAGAAGTCTGAAAAGGTCAGGG
CCCAGACTAAGGCTCTGACGTCTCCCCCCGGAGGGCAGCTCAGCACCGGCTCGGGCTAGGCCCTGACGTGTCCCCCTGAAGACAAATCAT
AAGCTCAGACCTCCGGGAAGCCACCAAGAACCACCCATTTCCTCCCCATGTTTGTCAAGCCGTCCTCAGGCGTTGACGACAACCCCTCAC
CTCAAAAAACTTTTCATGGCACGCATATGGCTCAATAAACTAGCAGGAGTCTATAAAGCGTGGAGACAGTTCAGGAGGGGGCTCGCATC
TCTCCTTCACGCGCCCGCCGCCCTACCTGAGGCCGCCATCCACGCCGGTTGAGTCGCGTTCTGCCGGCCTCCCGCCTGTGGTGCCTCCTGA
ACTGCCGTCCGCCGTCTAGGTAAGTTTAAAGCTCAGGTCGAGACCGGGCCTTTGTCCGGCGCTCCCTTGGAGCCTACCTAGACTCAGCCGG
```

CTCTCCACGCTTTGCCTGACCCTGCTTGCTCAACTCTACGTCTTTGTTTCGTTTTCTGTTCTGCGCCGTTACAGATCGAAAGTTCCACCC

CTTTCCCTTTCATTCACGACTGACTGCCGGCTTGGCCCACGGCCAAGTACCGGCGACTCCGTTGGCTCGGAGCCAGCGACAGCCCATCCT 9000

LTR—₁—cellular
ATAGCACTCTCAGGAGAGAAATTTAGTACACACATAGTTGGAGGTAG

About 3 μg of ATK-1 DNA was completely digested with 10 units of BamHI (product of BRL). This digest generates 3 fragments which were isolated and subcloned into pBR322 separately. A half of the digest (1.5 μg) was mixed with about 0.5 μg of pBR322 DNA digested with BamHI as mentioned above and the remaining half was mixed with about 0.5 μg of pBR322 DNA digested with the enzymes EcoRI and BamHI. The mixtures were subjected to reaction with T4 DNA ligase for 4 days. *Escherichia coli* C600 was transformed with each reaction solution by the method of Enea et al. [J. Mol. Biol., 96, 495–509 (1975)] and plasmids wherein three DNA fragments produced by BamHI treatment are cloned in pBR322 respectively were obtained as illustrated at the bottom of FIG. 1. The plasmid having the 5' terminal DNA fragment was named pATK03, the one having the middle fragment pATK06, and the one having the 3' terminal DNA fragment pATK08. Each plasmid was incorporated in *Escherichia coli* C600 strain and the strains having the plasmids were deposited on Nov. 23, 1982 with the American Type Culture Collection in U.S.A. as ATCC 39244, 39245 and 39246, respectively.

EXAMPLE 3

Use of λATK-1 for the diagnosis of human leukemia:
In this example, about 10 ml of the peripheral boood was obtained from leukemia patients and 0.5 ml of 10% SDS was added to dissolve the erythrocytes and lymphocytes. 0.15 ml of 100 mM EDTA and 400 μg of proteinase K were added and the mixture was allowed to react at 45° C. for 2 hours. The reaction solution was subjected to phenol extraction three times to extract DNA and the high molecular weight DNA was recovered by winding round a glass rod. Yield was about 50 μg. 5 μg of the obtained DNA was digested with 5 units of EcoRI by the method mentioned above. The digest was subjected to 1% agarose gel electrophoresis and DNA fragments were fixed on a nitrocellulose by the method of Southern [J. Mol. Biol., 98, 508 (1975)].

The novel recombinant phage DNA (λATK-1) obtained by the present invention was labelled with a nick translation kit (product of Amersham) in the presence of $^{32}$P-dCTP. The labelled DNA probe was hybridized with the cellulose DNA fragments on the nitrocellulose membrane mentioned above and the human leukemia virus genome was detected by autoradiography.

By the method described above, the human leukemi virus genome was detected in all the 18 cases diagnosed pathologically and clinically as adult T-cell leukemia.

What is claimed is:

1. A substantially pure viral genomic having a base sequence of:

Table 1.

TGACAATGACCATGAGCCCCAAATATCCCCCGGGGGCTTAGAGCCTCCCAGTGAAAAACATTTCCGAGAAACAGAAGTCTGAAAAGGTCA 90

GGGCCCAGACTAAGGCTCTGACGTCTCCCCCCGGAGGGCAGCTCAGCACCGGCTCGGGCTAGGCCCTGACGTGTCCCCCTGAAGACAAAT

CATAAGCTCAGACCTCCGGGAAGCCACCAAGAACCACCCATTTCCTCCCCATGTTTGTCAAGCCGTCCTCAGGCGTTGACGACAACCCCT

CACCTCAAAAAACTTTTCATGGCACGCATATGGCTCAATAAACTAGCAGGAGTCTATAAAAGCGTGGAGACAGTTCAGGAGGGGGCTCGG

ATCTCTCCTTCACGCGCCCGCCGCCCTACCTGAGGCCGCCATCCACGCCGGTTGAGTCGCGTTCTGCCGCCTCCCGCCTGTGGTGCCTCC

TGAACTGCGTCCGCCGTCTAGGTAAGTTTAAAGCTCAGGTCGAGACCGGGCCTTTGTCCGGCGCTCCCTTGGAGCCTACCTAGACTCAGC

CGGCTCTCCACGCTTTGCCTGACCCTGCTTGCTCAACTCTACGTCTTTGTTTCGTTTTCTGTTCTGCGCCGTTACAGATCGAAAGTTCCA

CCCCTTTCCCTTTCATTCACGACTGACTGCCGGCTTGGCCCACGGCCAAGTACCGGCGACTCCGTTGGCTCGGAGCCAGCGACAGCCCAT

CCTATAGCACTCTCAGGAGAGAAATTTAGTACACAGTTGGGGGCTCGTCCGGGATACGAGCGCCCCTTTATTCCCTAGGCAATGGGCCAA

ATCTTTTCCCGTAGCGCTAGCCCTATTCCGCGACCGCCCCGGGGGCTGGCCGTCATCACTGGCTTAACTTCCTCCAGGGGGCATATCGC 900

CTAGAACCCGGTCCCTCCAGTTACGATTTCCACCAGTTAAAAAAATTTCTTAAAATAGCTTTAGAAACACCGGCTCGGATCTGTCCCATT

AACTACTCCCTCCTAGCCAGCCTACTCCCAAAAGGATACCCCGGCCGGGTGAATGAAATTTTACACATACTCATCCAAACCCAAGCCCAG

ATCCCGTCCCGTCCCGCGCCACCGCCGCCGTCATCCCCCACCCACGACCCCCGGATTCTGATCCACAAATCCCCCTCCCTATGTTGAG

CCTACGGCCCCCCAAGTCCTTCCAGTCATGCATCCACATGGTGCTCCTCCTAACCATCGCCCATGGCAAATGAAAGACCTACAGGCCATT

AAGCAAGAAGTCTCCCAAGCAGCCCCTGGGAGCCCCCAGTTTATGCAGACCATCCGGCTTGCGGTGCAGCAGTTTGACCCCACTGCCAAA

GACCTCCAAGACCTCCTGCAGTACCTTTGCTCCTCCCTCGTGGCTTCCCTCCATCACCAGCAGCTAGATAGCCTTATATCAGAGGCCGAA

ACCCGAGGTATTACAGGTTATAACCCATTAGCCGGTCCCCTCCGTGTCCAAGCCAACAATCCACAACAACAAGGATTAAGGCGAGAATAC

CAGCAACTCTGGCTCGCCGCCTTCGCCGCCCTGCCGGGGAGTGCCAAAGACCCTTCCTGGGCCTCTATCCTCCAAGGCCTGGAGGAGCCT

TACCACGCCTTCGTAGAACGCCTCAACATAGCTCTTGACAATGGGCTGCCAGAAGGCACGCCCAAAGACCCCATCTTACGTTCCTTAGCC

TACTCCAATGCAAACAAAGAATGCCAAAAATTACTACAGGCCCGAGGACACACTAATAGCCCTCTAGGAGATATGTTGCGGGCTTGTCAG 1800

```
GGCCACTGGAGTCGGGACTGCACTCAGCCTCGTCCCCCCCCGGGCCATGCCCCTATGTCAAGACCCAACTCACTGGAAGCGAGACTGC
CCCCGCCTAAAGCCCACTATCCCAGAACCAGAGCCAGAGGAAGATGCCCTCCTATTAGACCTCCCCGCTGACATCCCACACCCAAAAAAC
TCCATAGGGGGGGAGGTTTAACCTCCCCCCCCACATTACAGCAAGTCCTTCCTAACCAAGACCCAGCATCTATTCTGCCAGTTATACCGT
TAGATCCCGCCCGTCGGCCCGTAATTAAAGCCCAGGTTGACACCCAGACCAGCCACCCAAAGACTATCGAAGCTTTACTAGATACAGGAG
CAGACATGACAGTCCTTCCGATAGCCTTGTTCTCAAGTAATACTCCCTCAAAAATACATCCGTATTAGGGGCAGGGGGCCAAACCCAAGA
TCACTTTAAGCTCACCTCCCTTCCTGTGCTAATACGCCTCCCTTTCCGGACAACGCCTATTGTTTAACATCTTGCCTAGTTGATACCAA
AAACAACTAGGCCATCATAGGTCGTGATGCCTTACAACAATGCCAAGGCGTCCTGTACCTCCCTGAGGCAAAAAGGCCGCCTGTAATCTT
GCCAATACAGGCGCCAGCCGTCCTTGGGCTAGAACACCTCCCAAGGCCCCCGAAATCAGCCAGTTCCCTTTAAACCAGAACGCCTCCAG
GCCTTGCAACACTTGGTCCGGAAGGCCCTGGAGGCAGGCCATATCGAACCCTACACCGGGCCAGGGAATAACCCAGTATTCCCAGTTAAA 2700
AAGCCAATGGAACCTGGCGATTCATCCACGACCTGCGGGCCACTAACTCTCTAACCATAGATCTCTCATCATCTTCCCCCGGGCCCCCT
GACTTGTCCAGCCTGCCAACCACACTAGCCCACTTGCAAACTATAGACCTTAGAGACGCCTTTTTCCAAATCCCCTTACCTAAACAGTTC
CAGCCCTACTTTGCTTTCACTGTCCCACAGCAGTGTAACTACGGCCCCGGCACTAGATACGCCTGGAAAGTACTACCCCAAGGGTTTAAA
AATAGTCCCACCCTGTTCGAAATGCAGCTGGCCCATATCCTGCAGCCCATTCGGCAAGCTTTCCCCCAATGCACTATTCTTCAGTACATG
GATGACATTCTCCTAGCAAGCCCCTCCCATGAGGACCTACTACTACTCTCAGAGGCCACAATGGCTTCCCTAATCTCCCATGGGTTGCCT
GTGTCCGAAAACAAAACCCAGCAAACCCCTGGAACAATTAAGTTCCTAGGGCAGATAATTTCACCCAATCACCTCACTTATGATGCAGTC
CCCACGGTACCTATACGGTCCCGCTGGGCGCTACCTGAACTTCAAGCCCTACTTGGCGAGATTCAGTGGGTCTCCAAAGGAACTCCTACC
TTACGCCAGCCCCTTCACAGTCTCTACTGTGCCTTACAAAGGCATACTGATCCCCGAGACCAAATATATTTAAATCCTTCTCAAGTTCAA
TCATTAGTGCAGCTGCGGCAGGCCCTGTCACAGAACTGCCGCAGTAGACTAGTCCAAACCCTGCCCCTCCTAGGGGCTATTATGCTGACC
CTCACTGGCACCACTACTGTAGTGTTCCAGTCCAAGCAGCAGTGGCCACTTGTCTGGCTACATGCCCCCTACCCCACACTAGCCAGTGC 3600
CCCTGGGGGCAGCTACTTGCCTCAGCTGTGTTATTACTCGACAAATACACCTTGCAATCCTATGGGCTGCTCTGCCAAACCATACATCAT
AACATCTCCACCCAAACCTTCAACCAATTCATTCAAACATCTGACCACCCCAGTGTTCCTATCTTACTCCACCACAGTCACCGATTCAAA
AATTTAGGTGCCCAAACTGGAGAACTTTGGAACACTTTTCTTAAAACAGCTGCCCCATTGGCTCCTGTGAAAGCCCTCATGCCAGTGTTT
ACTCTTTCCCCGGTGATTATAAACACCGCCCCTGCCTGTTTTCAGACGGATCTACCTCCCGGGCAGCCTATATTCTCTGGGACAAGCAA
ATATTGTCACAAAGATCATTCCCCCTTCCGCCACCGCACAAGTCGGCCCAACGGGCCGAACTTCTCGGACTTTTGCATGGCCTCTCCAGC
GCCCGTTCGTGGCGCTGTCTCAACATATTTCTAGACTCCAAGTATCTTTATCATTACCTTCGGACCCTTGCCCTGGGCACCTTCCAAGGC
AGGTCCTCTCAGGCCCCCTTTCAGGCCCTTCTGCCCCGCTTACTATCGCGTAAGGTCGTCTATTTGCACCACGTTCGCAGCCATACCAAT
CTACCTGATCCCATCTCCAGGCTCAACGCTCTCACAGATGCCCTACTAATCACCCCTGTCCTGCAGCTCTCTCCTGCAGAACTACACAGT
TTCACCCATTGCGGACAGACGGCCCTCACATTGCAAGGGGCAACCACAACTGAGGCTTCCAATATCCTGCGCTCTTGCCACGCCTGCCGC
GGAGGCAACCCACAACATCAGATGCCTCGGGGACACATCCGCCGTGGCCTACTTCCTAACCACATCTGGCAAGGCGACATTACCCATTTC 4500
AAATATAAAAATACGCTGTATCGCCTTCATGTATGGGTAGACACCTTTTCAGGAGCCATCTCAGCTACCCAAAAGAGAAAAGAAACAAGC
TCAGAAGCTATTTCCTCTTTGCTTCAGGCCATTGCCCATCTAGGCAAGCCTAGCTACATAAACACAGACAACGGCCCTGCCTATATTTCC
CAAGACTTCCTCAATATGTGTACCTCCCTTGCTATTCGCCATACCACCCATGTCCCCTACAATCCAACCAGCTCAGGACTTGTAGAACGC
TCTAATGGCATTCTTAAAACCCTATTATATAAGTACTTTACTGACAAAACCCGACCTACCCATGGATAATGCTCTATCCATAGCCCTATGG
ACAATCAACCACCTGAATGTGTTAACCAACTGCCACAAAACCCGATGGCAGCTTCACCACTCCCCCCGACTCCAGCCGATCCCAGAGACA
CGTTCCCTCAGCAATAAACAAACCCATTGGTATTATTTCAAGCTTCCTGGTCTTAATAGCCGCCAGTGGAAAGGACCACAGGAGGCTCTC
CAAGAAGCTGCCGGCGCTGCTCTCATCCCGGTAAGCGCTAGTTCTGCCCAGTGGATCCCGTGGAGACTCCTCAAGCGAGCTGCATGCCCA
AGACCCGTCGGAGGCCCCGCCGATCCCAAAGAAAAAGACCTCCAACACCATGGGTAAGTTTCTCGCCACTTTGATTTTATTCTTCCAGTT
CTGCCCCTCATCTTCGGTGATTACAGCCCCAGCTGCTGTACTCTCACAATTGGAGTCTCCTCATACCACTCTAAACCCTGCAATCCTGC
CCAGCCAGTTTGTTCGTGGACCCTCGACCTGCTGGCCCTTCAGCAGATCAGGCCCTACAGCCCCCGTGCCCTAACCTAGTAAGTTACTC 5400
CAGCTACCATGCCACCTATTCCCTATATCTATTCCCTCATTGGACTAAGAAGCCAAACCGAAATGGCGGAGGCTATTATTCAGCCTCTTA
TTCAGACCCTTGTTCCTTAAAGTGCCCATACCTGGGGTGCCAATCATGGACCCTGCCCCTATACAGGAGCCGTCTCCAGCCCCTACTGGAA
GTTTCAACACGATGTCAATTTTACTCAAGAAGTTTCACGCCTCAATATTAATCTCCATTTTTCAAAATGCGGTTTTCCCTTCTCCCTTCT
AGTCGACGCTCCAGGATATGACCCCATCTGGTTCCTTAATACCGAACCCAGCCAACTGCCTCCCACCGCCCCTCCTCTACTCCCCACTC
TAACCTAGACCACATCCTCGAGCCCTCTATACCATGGAAATCAAAACTCCTGACCCTTGTCCAGTTAACCCTACAAAGCACTAATTATAC
```

```
TTGCATTGTCTGTATCGATCGTGCCAGCCTCTCCACTTGGCACGTCCTATACTCTCCCAACGTCTCTGTTCCATCCTCTTCTTCTACCCC
CCTCCTTTACCCATCGTTAGCCGCTTCCAGCCCCCACCTGACGTTACCATTTAACTGGACCCACTGCTTTGACCCCCAGATTCAAGCTAT
AGTCTCCTCCCCCTGTCATAACTCCCTCATCCTGCCCCCCTTTTCCTTGTCACCTGTTCCCACCCTAGGATCCCGCTCCCGCCGAGCGGT
ACCGGTGGCGGTCTGGCTTGTCTCCGCCCTGCCCATGGGAGCCGGAGTGGCTGGCGGGATTACCGGCTCCATGTCCCTCGCCTCAGGAAA
GAGCCTCCTACATGAGGTGGACAAAGATATTTCCCAGTTAACTCAAGCAATAGTCAAAAACCACAAAAATCTACTCAAAATTGCGCAGTA 6300
TGCTGCCCAGAACAGACGAGGCCTTGATCTCCTGTTCTGGGAGCAAGGAGGATTATGCAAAGCATTACAAGAACAGTGCCGTTTTCCGAA
TATTACCAATTCCCATGTCCCAATACTACAAGAAAGACCCCCCTTGAGAATCGAGTCCTGACTGGCTGGGGCCTTAACTGGGACCTTGG
CCTCTCACAGTGGGCTCGAGAGGCCTTACAAACTGGAATCACCCTTGTTGCGCTACTCCTTCTTGTTATCCTTGCAGGACCATGCATCCT
CCGTCAGCTACGACACCTCCCCTCGCGCGTCAGATACCCCCATTACTCTCTTATAAAACCTGAGTCATCCCTGTAAACCAAGCACGCAAT
TATTGCAACCACATCGCCTCCAGCCTCCCCTGCCAATAATTAACCTCTCCCATCAAATCCTCCTTCTCCTGCAGCAACTTCCTCCGTTCA
GCCTCCAAGGACTCCACCTCGCCTTCCAACTGTCTAGTATAGCCATCAATCCCCAACTCCTGCATTTTTTCTTTCCTAGCACTATGCTGT
TTCGCCTTCTCAGCCCCTTGTCTCCACTTGCGCTCACGGCGCTCCTGCTCTTCCTGCTTCCTCCTAGCGACGTCAGCGGCCTTCTTCTCC
GCCCGCCTCCTGCGCCGTGCCTTCTCCTCTTCCTTCCTTTTCAAATACTCAGCGGTCTGCTTTTCCTCCTCTTTCTCCCGCTCTTTTTTT
CGCTTCCTCTTCTCCTCAGCCCGTCGCTGCCGATCACGATGCGTTTCCCCGCGAGGTGGCGCTTTCTCCCTGGAGGGCCCCGTCGCAGC
CGGCCGCGGCTTTCCTCTTCTAAGGATAGCAAACCGTCAAGCACAGCTTCCTCCTCCTCCTTGTCCTTTAACTCTTCCTCCAAGGATAAT 7200
AGCCCGTCCACCAATTCCTCCACCAGCAGGTCCTCCGGGCATGACACAGGCAAGCATCGAAACAGCCCTGCAGATACAAAGTTAACCATG
CTTATTATCAGCCCACTTCCCAGGGTTTGGACAGAGTCTTCTTTTCGGATACCCAGTCTACGTGTTTGGAGACTGTGTACAAGGCGACTG
GTCCCCATCTCTGGGGGACTATGTTCGGCCCGCCTACATCGTCACGCCCTACTGGCCACCTGTCCAGAGCATCAGATCACCTGGACCC
CATCGATGGACGCGTTATCGGCTCAGCTCTACAGTTCCTTATCCCTCGACTCCCCTCCTTCCCCACCCAGAGAACCTCTAAGACCCTCAA
GGTCCTTACCCCGCCAATCACTCATACAACCCCCAACATTCCACCCTCCTTCCTCCAGGCCATGCGCAAATACTCCCCCTTCCGAAATGG
ATACATGGAACCCACCCTTGGGCAGCACCTCCCAAGCCTGTCTTTTCCAGACCCCGGACTCCGGCCCCAAAACCTGTACACCCTCTGGGG
AGGCTCCGTTGTCTGCATGTACCTCTACCAGCTTTCCCCCCCCATCACCTGGCCCCTCCTGCCCCACGTGATTTTTTGCCACCCCGGCCA
GCTCGGGGCCTTCCTCACCAATGTTCCCTACAAGCGAATAGAAGAACTCCTCTATAAAATTTCCCTCACCACAGGGGCCCTAATAATTCT
ACCCGAAGACTGTTTGCCCACCACCCTTTTCCAGCCTGCTAGGGCACCCGTCACGCTAACAGCCTGGCAAAACGGCCTCCTTCCGTTCCA
CTCAACCCTCACCACTCCAGGCCTTATTTGGACATTTACCGATGGCACGCCTATGATTTCCGGGCCCTGCCCTAAAGATGGCCAGCCATC 8100
TTTAGTACTACAGTCCTCCTCCTTTATATTTCACAAATTTCAAACCAAGGCCTACCACCCCTCATTTCTACTCTCACACGGCCTCATACA
GTACTCTTCCTTTCATAGTTTACATCTCCTGTTTGAAGAATACACCAACATCCCCATTTCTCTACTTTTTAACGAAAAAGAGGCAGATGA
CAATGACCATGAGCCCCAAATATCCCCCGGGGGCTTAGAGCCTCCCAGTGAAAAACATTTCCGAGAAACAGAAGTCTGAAAAGGTCAGGG
CCCAGACTAAGGCTCTGACGTCTCCCCCCGGAGGGCAGCTCAGCACCGGCTCGGGCTAGGCCCTGACGTGTCCCCCTGAAGACAAATCAT
AAGCTCAGACCTCCGGGAAGCCACCAAGAACCACCCATTTCCTCCCCATGTTTGTCAAGCCGTCCTCAGGCGTTGACGACAACCCCTCAC
CTCAAAAAACTTTTCATGGCACGCATATGGCTCAATAAACTAGCAGGAGTCTATAAAAGCGTGGAGACAGTTCAGGAGGGGGCTCGCATC
TCTCCTTCACGCGCCCGCCGCCCTACCTGAGGCCGCCATCCACGCCGGTTGAGTCGCGTTCTGCCGCCTCCCGCCTGTGGTGCCTCCTGA
ACTGCGTCCGCCGTCTAGGTAAGTTTAAAGCTCAGGTCGAGACCGGGCCTTTGTCCGGCGCTCCCTTGGAGCCTACCTAGACTCAGCCGG
CTCTCCACGCTTTGCCTGACCCTGCTTGCTCAACTCTACGTCTTTGTTTCGTTTTCTGTTCTGCGCCGTTACAGATCGAAAGTTCCACCC
CTTTCCCTTTCATTCACGACTGACTGCCGGCTTGGCCCACGGCCAAGTACCGGCGACTCCGTTGGCTCGGAGCCAGCGACAGCCCATCCT 9000
ATAGCACTCTCAGGAGAGAAATTTAGTACACA.
```

2. A recombinant DNA vector harboring a viral genomic DNA, wherein the viral genomic DNA has a base sequence of:

```
TGACAATGACCATGAGCCCCAAATATCCCCCGGGGGCTTAGAGCCTCCCAGTGAAAAACATTTCCGAGAAACAGAAGTCTGAAAAGGTCA 90
GGGCCCAGACTAAGGCTCTGACGTCTCCCCCCGGAGGGCAGCTCAGCACCGGCTCGGGCTAGGCCCTGACGTGTCCCCCTGAAGACAAAT
```

```
CATAAGCTCAGACCTCCGGGAAGCCACCAAGAACCACCCATTTCCTCCCCATGTTTGTCAAGCCGTCCTCAGGCGTTGACGACAAACCCCT
CACCTCAAAAAACTTTTCATGGCACGCATATGGCTCAATAAACTAGCAGGAGTCTATAAAAGCGTGGAGACAGTTCAGGAGGGGGCTCGC
ATCTCTCCTTCACGCGCCCGCCGCCCTACCTGAGGCCGCCATCCACGCCGGTTGAGTCGCGTTCTGCCGCCTCCCGCCTGTGGTGCCTCC
TGAACTGCGTCCGCCGTCTAGGTAAGTTTAAAGCTCAGGTCGAGACCGGGCCTTTGTCCGGCGCTCCCTTGGAGCCTACCTAGACTCAGC
CGGCTCTCCACGCTTTGCCTGACCCTGCTTGCTCAACTCTACGTCTTTGTTTCGTTTTCTGTTCTGCGCCGTTACAGATCGAAAGTTCCA
CCCCTTTCCCTTTCATTCACGACTGACTGCCGGCTTGGCCCACGGCCAAGTACCGGCGACTCCGTTGGCTCGGAGCCAGCGACAGCCCAT
CCTATAGCACTCTCAGGAGAGAAATTTAGTACACAGTTGGGGGCTCGTCCGGGATACGAGCGCCCCTTTATTCCCTAGGCAATGGGCCAA
ATCTTTTCCCGTAGCGCTAGCCCTATTCCGCGACCGCCCCGGGGGCTGGCCGCTCATCACTGGCTTAACTTCCTCCAGGCGGCATATCGC  900
CTAGAACCCGGTCCCTCCAGTTACGATTTCCACCAGTTAAAAAAATTTCTTAAAATAGCTTTAGAAACACCGGCTCGGATCTGTCCCATT
AACTACTCCCTCCTAGCCAGCCTACTCCCAAAAGGATACCCCGGCCGGGTGAATGAAATTTTACACATACTCATCCAAACCCAAGCCCAG
ATCCCGTCCCGTCCCGGCCACCGCCGCCGTCATCCCCCACCCACGACCCCCGGATTCTGATCCACAAATCCCCCTCCCTATGTTGAG
CCTACGGCCCCCCAAGTCCTTCCAGTCATGCATCCACATGGTGCTCCTCCTAACCATCGCCCATGGCAAATGAAAGACCTACAGGCCATT
AAGCAAGAAGTCTCCCAAGCAGCCCCTGGGAGCCCCCAGTTTATGCAGACCATCCGGCTTGCGGTGCAGCAGTTTGACCCCACTGCCAAA
GACCTCCAAGACCTCCTGCAGTACCTTTGCTCCTCCCTCGTGGCTTCCCTCCATCACCAGCAGCTAGATAGCCTTATATCAGAGGCCGAA
ACCCGAGGTATTACAGGTTATAACCCATTAGCCGGTCCCCTCCGTGTCCAAGCCAACAATCCACAACAACAAGGATTAAGGCGAGAATAC
CAGCAACTCTGGCTCGCCGCCTTCGCCGGCCTGCCGGGGAGTGCCAAAGACCCTTCCTGGGCCTCTATCCTCCAAGGCCTGGAGGAGCCT
TACCACGCCTTCGTAGAACGCCTCAACATAGCTCTTGACAATGGGCTGCCAGAAGGCACGCCCAAAGACCCCATCTTACGTTCCTTAGCC
TACTCCAATGCAAACAAAGAATGCCAAAAATTACTACAGGCCCGAGGACACACTAATAGCCCTCTAGGAGATATGTTGCGGGCTTGTCAG 1800
ACCTGGACCCCCAAAGACAAAACCAAAGTGTTAGTTGTCCAGCCTAAAAACCCCCCCAAATCAGCCGTGCTTCCGGTGCGGGAAAGCA
GGCCACTGGAGTCGGGACTGCACTCAGCCTCGTCCCCCCCCGGGCCATGCCCCCTATGTCAAGACCCAACTCACTGGAAGCGAGACTGC
CCCCGCCTAAAGCCCACTATCCCAGAACCAGAGCCAGAGGAAGATGCCCTCCTATTAGACCTCCCCGCTGACATCCCACACCCAAAAAAC
TCCATAGGGGGGGAGGTTTAACCTCCCCCCCCACATTACAGCAAGTCCTTCCTAACCAAGACCCAGCATCTATTCTGCCAGTTATACCGT
TAGATCCCGCCCGTCGGCCCGTAATTAAAGCCCAGGTTGACACCCAGACCAGCCACCCAAAGACTATCGAAGCTTTACTAGATACAGGAG
CAGACATGACAGTCCTTCCGATAGCCTTGTTCTCAAGTAATACTCCCTCAAAAATACATCCGTATTAGGGGCAGGGGGCCAAACCCAAGA
TCACTTTAAGCTCACCTCCCTTCCTGTGCTAATACGCCTCCCTTTCCGGACAACGCCTATTGTTTTAACATCTTGCCTAGTTGATACCAA
AAACAACTAGGCCATCATAGGTCGTGATGCCTTACAACAATGCCAAGGCGTCCTGTACCTCCCTGAGGCAAAAAGGCCGCCTGTAATCTT
GCCAATACAGGCGCCAGCCGTCCTTGGGCTAGAACACCTCCCAAGGCCCCCGAAATCAGCCAGTTCCCTTTAAACCAGAACGCCTCCAG
GCCCTTGCAACACTTGGTCCGGAAGGCCCTGGAGGCAGGCCATATCGAACCCTACACCGGGCCAGGGAATAACCCAGTATTCCCAGTTAAA 2700
AAGGCCAATGGAACCTGCCGATTCATCCACGACCTGCCGGGCCACTAACTCTCTAACCATAGATCTCTCATCATCTTCCCCCGGGCCCCCT
GACTTGTCCAGCCTGCCAACCACACTAGCCCACTTGCAAACTATAGACCTTAGAGACGCCTTTTTCCAAATCCCCTTACCTAAACAGTTC
CAGCCCTACTTTGCTTTCACTGTCCCACAGCAGTGTAACTACGGCCCCGGCACTAGATACGCCTGGAAAGTACTACCCCAAGGGTTTAAA
AATAGTCCCACCCTGTTCGAAATGCAGCTGGCCCATATCCTGCAGCCCATTCGGCAAGCTTTCCCCCAATGCACTATTCTTCAGTACATG
GATGACATTCTCCTAGCAAGCCCCTCCCATGAGGACCTACTACTACTCTCAGAGGCCACAATGGCTTCCCTAATCTCCCATGGGTTGCCT
GTGTCCGAAAACAAAACCCAGCAAACCCCTGGAACAATTAAGTTCCTAGGGCAGATAATTTCACCCAATCACCTCACTTATGATGCAGTC
CCCACGGTACCTATACGGTCCCGCTGGGCGCTACCTGAACTTCAAGCCCTACTTGGCGAGATTCAGTGGGTCTCCAAAGGAACTCCTACC
TTACGCCAGCCCCTTCACAGTCTCTACTGTGCCTTACAAAGGCATACTGATCCCCGAGACCAAATATATTTAAATCCTTCTCAAGTTCAA
TCATTAGTGCAGCTGCCGGCAGGCCCTGTCACAGAACTGCCGCAGTAGACTAGTCCAAACCCTGCCCCTCCTAGGGGCTATTATGCTGACC
CTCACTGGCACCACTACTGTAGTGTTCCAGTCCAAGCAGCAGTGGCCACTTGTCTGGCTACATGCCCCCCTACCCCACACTAGCCAGTGC 3500
CCCTGGGGGCAGCTACTTGCCTCAGCTGTGTTATTACTCGACAAATACACCTTGCAATCCTATGGGCTGCTCTGCCAAACCATACATCAT
AACATCTCCACCCAAACCTTCAACCAATTCATTCAAACATCTGACCACCCCAGTGTTCCTATCTTACTCCACCACAGTCACCGATTCAAA
AATTTAGGTGCCCAAACTGGAGAACTTTGGAACACTTTTCTTAAAACAGCTGCCCCATTGGCTCCTGTGAAAGCCCTCATGCCAGTGTTT
ACTCTTTCCCCGGTGATTATAAACACCGCCCCTGCCTGTTTTCAGACGGATCTACCTCCCGGGCAGCCTATATTCTCTGGGACAAGCAA
ATATTGTCACAAAGATCATTCCCCCTTCCGCCACCGCACAAGTCGGCCCAACGGGCCGAACTTCTCGGACTTTTGCATGGCCTCTCCAGC
GCCCGTTCGTGGCGCTGTCTCAACATATTTCTAGACTCCAAGTATCTTTATCATTACCTTCGGACCCTTGCCCTGGGCACCTTCCAAGGC
```

```
AGGTCCTCTCAGGCCCCCTTTCAGGCCCTTCTGCCCCGCTTACTATCGCGTAAGGTCGTCTATTTGCACCACGTTCGCAGCCATACCAAT
CTACCTGATCCCATCTCCAGGCTCAACGCTCTCACAGATGCCCTACTAATCACCCCTGTCCTGCAGCTCTCTCCTGCAGAACTACACAGT
TTCACCCATTGCGGACAGACGGCCCTCACATTGCAAGGGGCAACCACAACTGAGGCTTCCAATATCCTGCGCTCTTGCCACGCCTGCCGC
GGAGGCAACCCACAACATCAGATGCCTCGGGGACACATCCGCCGTGGCCTACTTCCTAACCACATCTGGCAAGGCGACATTACCCATTTC 4500
AAATATAAAAATACGCTGTATCGCCTTCATGTATGGGTAGACACCTTTTCAGGAGCCATCTCAGCTACCCAAAAGAGAAAAGAAACAAGC
TCAGAAGCTATTTCCTCTTTGCCTTCAGGCCATTGCCCATCTAGGCAAGCCTAGCTACATAAACACAGACAACGGCCCTGCCTATATTTCC
CAAGACTTCCTCAATATGTGTACCTCCCTTGCTATTCGCCATACCACCCATGTCCCCTACAATCCAACCAGCTCAGGACTTGTAGAACGC
TCTAATGGCATTCTTAAAACCCTATTATATAAGTACTTTACTGACAAACCCGACCTACCCATGGATAATGCTCTATCCATAGCCCTATGG
ACAATCAACCACCTGAATGTGTTAACCAACTGCCACAAAACCCGATGGCAGCTTCACCACTCCCCCCGACTCCAGCCGATCCCAGAGACA
CGTTCCCTCAGCAATAAACAAACCCATTGGTATTATTTCAAGCTTCCTGGTCTTAATAGCCGCCAGTGGAAAGGACCACAGGAGGCTCTC
CAAGAAGCTGCCGGCGCTGCTCTCATCCCGGTAAGCGCTAGTTCTGCCCAGTGGATCCCGTGGAGACTCCTCAAGCGAGCTGCATGCCCA
AGACCCGTCGGAGGCCCCGCCGATCCCAAAGAAAAGACCTCCAACACCATGGGTAAGTTTCTCGCCACTTTGATTTTATTCTTCCAGTT
CTGCCCCCTCATCTTCGGTGATTACAGCCCCAGCTGCTGTACTCTCACAATTGGAGTCTCCTCATACCACTCTAAACCCTGCAATCCTGC
CCAGCCAGTTTGTTCGTGGACCCTCGACCTGCTGGCCCTTTCAGCAGATCAGGCCCTACAGCCCCCGTGCCCTAACCTAGTAAGTTACTC 5400
CAGCTACCATGCCACCTATTCCCTATATCTATTCCCTCATTGGACTAAGAAGCCAAACCGAAATGGCGGAGGCTATTATTCAGCCTCTTA
TTCAGACCCTTGTTCCTTAAAGTGCCCATACCTGGGGTGCCAATCATGGACCTGCCCCTATACAGGAGCCGTCTCCAGCCCCTACTGGAA
GTTTCAACACGATGTCAATTTTACTCAAGAAGTTTCACGCCTCAATATTAATCTCCATTTTTCAAAATGCGGTTTTCCCTTCTCCCTTCT
AGTCGACGCTCCAGGATATGACCCCATCTGGTTCCTTAATACCGAAACCCAGCCAACTGCCTCCCACCGCCCTCCTCTACTCCCCCACTC
TAACCTAGACCACATCCTCGAGCCCTCTATACCATGGAAATCAAAAACTCCTGACCCTTGTCCAGTTAACCCTACAAAGCACTAATTATAC
TTGCATTGTCTGTATCGATCGTGCCAGCCTCTCCACTTGGCACGTCCTATACTCTCCCAACGTCTCTGTTCCATCCTCTTCTTCTACCCC
CCTCCTTTACCCATCGTTAGCGCTTCCAGCCCCCCACCTGACGTTACCATTTAACTGGACCCACTGCTTTGACCCCCAGATTCAAGCTAT
AGTCTCCTCCCCTGTCATAACTCCCTCATCCTGCCCCCCTTTTCCTTGTCACCTGTTCCCACCCTAGGATCCCGCTCCCGCCGAGCGGT
ACCGGTGGCGGTCTGGCTTGTGTCCGCCCTGCCCATGGGAGCCGGAGTGGCTGGCGGGATTACCGGCTCCATGTCCCTCGCCTCAGGAAA
GAGCCTCCTACATGAGGTGGACAAAGATATTTCCCAGTTAACTCAAGCAATAGTCAAAAACCACAAAAATCTACTCAAAATTGCGCAGTA 6300
TGCTGCCCAGAACAGACGAGGCCTTGATCTCCTGTTCTGGGAGCAAGGAGGATTATGCAAAGCATTACAAGAACAGTGCCGTTTTCCGAA
TATTACCAATTCCCATGTCCCAATACTACAAGAAAGACCCCCCCTTGAGAATCGAGTCCTGACTGGCTGGGGCCTTAACTGGGACCTTGG
CCTCTCACAGTGGGCTCGAGAGGCCTTACAAACTGGAATCACCCTTGTTGCGCTACTCCTTCTTGTTATCCTTGCAGGACCATGCATCCT
CCGTCAGCTACGACACCTCCCCTCGCGCGTCAGATACCCCCATTACTCTCTTATAAAACCTGAGTCATCCCTGTAAACCAAGCACGCAAT
TATTGCAACCACATCGCCTCCAGCCTCCCCTGCCAATAATTAACCTCTCCCATCAAATCCTCCTTCTCCTGCAGCAACTTCCTCCGTTCA
GCCTCCAAGGACTCCACCTCGCCTTCCAACTGTCTAGTATAGCCATCAATCCCCAACTCCTGCATTTTTCTTTCCTAGCACTATGCTGT
TTCGCCTTCTCAGCCCCTTGTCTCCACTTGCGCTCACGGCGCTCCTGCTCTTCCTGCTTCCTCCTAGCGACGTCAGCGGCCTTCTTCTCC
GCCCGCCTCCTGCGCCGTGCCTTCTCCTCTTCCTTCCTTTTCAAATACTCAGCGGTCTGCTTTTCCTCCTCTTTCTCCCGGCTCTTTTTT
CGCTTCCTCTTCTCCTCAGCCCGTCGCTGCCGATCACGATGCGTTTCCTCGCGAGGTGGCGCTTCTCCCCTGGAGGGCCCCGTCGCAGC
CGGCCGCGGCTTTCCTCTTCTAAGGATAGCAAACCGTCAAGCACAGCTTCCTCCTCCTCCTTGTCCTTTAACTCTTCCTCCAAGGATAAT 7200
AGCCCGTCCACCAATTCCTCCACCAGCAGGTCCTCCGGGCATGACACAGGCAAGCATCGAAACAGCCCTGCAGATACAAAGTTAACCATG
CTTATTATCAGCCCACTTCCCAGGGTTTGGACAGAGTCTTCTTTTCGGATACCCAGTCTACGTGTTTGGAGACTGTGTACAAGGCGACTG
GTGCCCCATCTCTGGGGGACTATGTTCGGCCCGCCTACATCGTCACGCCCTACTGGCCACCTGTCCAGAGCATCAGATCACCTGGGACCC
CATCGATGGACGCGTTATCGGCTCAGCTCTACAGTTCCTTATCCCTCGACTCCCCTCCTTCCCCACCCAGAGAACCTCTAAGACCCTCAA
GGTCCTTACCCCGCCAATCACTCATACAACCCCAACATTCCACCCTCCTTCCTCCAGGCCATGCGCAAATACTCCCCCTTCCGAAATGG
ATACATGGAACCCACCCTTGGGCAGCACCTCCCAACCCTGTCTTTTCCAGACCCCGGACTCCGGCCCCAAAACCTGTACACCCTCTGGGG
AGGCTCCGTTGTCTGCATGTACCTCTACCAGCTTTCCCCCCCCATCACCTGGCCCCTCCTGCCCACGTGATTTTTGCCACCCCGGCCA
GCTCGGGGCCTTCCTCACCAATGTTCCCTACAAGCGAATAGAAGAACTCCTCTATAAAATTTCCCTCACCACAGGGGCCCTAATAATTCT
ACCCGAAGACTGTTTGCCCACCACCCTTTTCCAGCCTGCTAGGGCACCCGTCACGCTAACAGCCTGGCAAAACGGCCTCCTTCCGTTCCA
CTCAACCCCTCACCACTCCAGGCCTTATTTGGACATTTACCGATGGCACGCCTATGATTTCCGGGCCCTGCCCTAAAGATGGCCAGCCATC 8100
```

21                                                                                    22

TTTAGTACTACAGTCCTCCTCCTTTATATTTCACAAATTTCAAACCAAGGCCTACCACCCCTCATTTCTACTCTCACACGGCCTCATACA
GTACTCTTCCTTTCATAGTTTACATCTCCTGTTTGAAGAATACACCAACATCCCCATTTCTCTACTTTTTAACGAAAAAGAGGCAGATGA
CAATGACCATGAGCCCCAAATATCCCCCGGGGGCTTAGAGCCTCCCAGTGAAAAACATTTCCGAGAAACAGAAGTCTGAAAAGGTCAGGG
CCCAGACTAAGGCTCTGACGTCTCCCCCCGGAGGGCAGCTCAGCACCGGCTCGGGCTAGGCCCTGACGTGTCCCCCTGAAGACAAATCAT
AAGCTCAGACCTCCGGGAAGCCACCAAGAACCACCCATTTCCTCCCCATGTTTGTCAAGCCGTCCTCAGGCGTTGACGACAACCCCTCAC
CTCAAAAAACTTTTCATGGCACGCATATGGCTCAATAAACTAGCAGGAGTCTATAAAAGCGTGGAGACAGTTCAGGAGGGGGCTCGCATC
TCTCCTTCACGCGCCCGCCGCCCTACCTGAGGCCGCCATCCACGCCGGTTGAGTCGCGTTCTGCCGCCTCCCGCCTGTGGTGCCTCCTGA
ACTGCGTCCGCCGTCTAGGTAAGTTTAAAGCTCAGGTCGAGACCGGGCCTTTGTCCGGCGCTCCCTTGGAGCCTACCTAGACTCAGCCGG
CTCTCCACGCTTTGCCTGACCCTGCTTGCTCAACTCTACGTCTTTGTTTCGTTTTCTGTTCTGCGCCGTTACAGATCGAAAGTTCCACCC
CTTTCCCTTTCATTCACGACTGACTGCCGGCTTGGCCCACGGCCAAGTACCGGCGACTCCGTTGGCTCGGAGCCAGCGACAGCCCATCCT 2000
ATAGCACTCTCAGGAGAGAAATTTAGTACACA.

\* \* \* \* \*

UNITED STATES PATENT AND TRADEMARK OFFICE
CERTIFICATE OF CORRECTION

PATENT NO. : 4,778,756
DATED : October 18, 1988
INVENTOR(S) : MITSUAKI YOSHIDA, ET AL.

It is certified that error appears in the above-identified patent and that said Letters Patent is hereby corrected as shown below:

Columns 11-12, following line 40, the heading "Table 1." should be deleted;

Column 12, line 32, "genomic having" should read: --genomic DNA having--.

Columns 13-14, before line 1, insert:

--ACCTGGACCCCCAAAGACAAAACCAAAGTGTTAGTTGTCCAGCCTAAAAAACCCCCCC CAAATCAGCCGTGCTTCCGGTGCGGGAAAGCA--;

Column 11, line 45 to Column 16, line 55, the underscoring should be deleted;

Column 15 line 68 to Column 22, line 20, the underscoring should be deleted.

Signed and Sealed this

Twenty-third Day of May, 1989

*Attest:*

DONALD J. QUIGG

*Attesting Officer*     *Commissioner of Patents and Trademarks*